United States Patent [19]

Heil, Jr.

[11] Patent Number: 5,041,107

[45] Date of Patent: Aug. 20, 1991

[54] ELECTRICALLY CONTROLLABLE, NON-OCCLUDING, BODY IMPLANTABLE DRUG DELIVERY SYSTEM

[75] Inventor: Ronald W. Heil, Jr., Roseville, Minn.

[73] Assignee: Cardiac Pacemakers, Inc., St. Paul, Minn.

[21] Appl. No.: 418,249

[22] Filed: Oct. 6, 1989

[51] Int. Cl.$^5$ ................................................. A61N 1/30
[52] U.S. Cl. ............................... 604/891.1; 604/892.1
[58] Field of Search ............... 604/890.1, 891.1, 892.1, 604/19–21; 417/48

[56] References Cited

U.S. PATENT DOCUMENTS

| | | |
|---|---|---|
| 3,731,681 | 5/1973 | Blackshear et al. . |
| 3,894,538 | 7/1975 | Richter .......................... 604/891.001 |
| 3,896,806 | 7/1975 | Wichterle . |
| 3,923,060 | 12/1975 | Ellinwood, Jr. . |
| 3,923,426 | 12/1975 | Theeuwes . |
| 3,951,147 | 4/1976 | Tucker et al. . |
| 4,014,334 | 3/1977 | Theeuwes et al. . |
| 4,140,121 | 2/1979 | Kühl et al. . |
| 4,373,527 | 2/1983 | Fischell . |
| 4,639,244 | 1/1987 | Rizk et al. ...................... 604/891.001 |
| 4,744,787 | 5/1988 | Phipps et al. . |

OTHER PUBLICATIONS

Studies on Surgical Adjuvant Chemotherapy for Colorectal Cancer and Administration of Neocarzinostatin into the Lumen of the Colon or Rectum Using a Double Balloon Catheter and Iontophoresis, by Shunji Akao, Arch. Jpn. Chir 50:67–82, Jan. 1981.

Drug Pacemakers in the Treatment of Heart Block by Judah Folkman et al, Annals of The New York Academy of Sciences, 1964, p. 857.

Improved Catheter Patency by Means of a Simple Check-Valve Mechanism by Rupp et al, vol. XXIX, Trans. Am. Soc. Artif. Intern. Organs, 1983, p. 275.

*Primary Examiner*—William E. Kamm
*Assistant Examiner*—Kevin Pontius
*Attorney, Agent, or Firm*—Haugen and Nikolai

[57] ABSTRACT

An implantable apparatus for continuous or periodic introduction of a drug to a desired release point in the body comprises an implantable power source and an elongated flexible plastic tubular catheter having a lumen filled with the drug to be delivered and containing therein a first device electrode. The distal end of the catheter is closed and located near the distal end is a port which extends through the wall of the catheter to communicate with the lumen. Just proximal of the port is a surface electrode mounted on the exterior wall of the catheter body. Extending through the catheter and joined to the drive electrode and the surface electrode are conductors which couple those electrodes to the implanted power source. Energization of the electrodes with a predetermined direct current potential causes a flow of the ionized drug molecules out through the port and into the area surrounding the surface electrode.

11 Claims, 1 Drawing Sheet

ELECTRICALLY CONTROLLABLE, NON-OCCLUDING, BODY IMPLANTABLE DRUG DELIVERY SYSTEM

BACKGROUND OF THE INVENTION

I. Field of the Invention

This invention relates generally to medical apparatus for the long-term delivery of medicaments to a desired release site within the body, and more particularly to an implantable drug delivery system which is electrochemical in nature and contains no moving parts.

II. Discussion of the Prior Art

In the treatment of certain diseases, it is desirable to administer various drugs to predetermined points within the body where the drug is effective in treating the disease process, but without burdening the rest of the body. For example, in the treatment of certain cancers, chemotherapy may be effective in killing the cancer cells but those same drugs may have serious effects on normal cells as well. Thus, they cannot be administered by way of a bolus injection into the vascular system and with reliance upon the blood circulation to carry the drug to the cancer site. In another example, certain drugs are effective in treating cardiac arrhythmias and it is desirable to deliver those drugs directly to the heart while minimizing or completely eliminating undesirable side effects. An effective drug pump is also invaluable to diabetics who must have one or more injections daily of insulin. The need to carry around a kit and to inject oneself with a hypodermic needle on this frequent basis is unpleasant at best and leads to problems with patient compliance.

The foregoing problems have been addressed by the prior art and, in this regard, reference is made to the Fischell U.S. Pat. No. 4,373,527 and the Blackshear et al U.S. Pat. No. 3,731,681. Each of these patents describes an implantable pump having a reservoir for storing a quantity of a liquid drug adequate to satisfy the patient's needs over a relatively long time period.

The Blackshear pump includes a housing divided into two fluid-type chambers with a pressurized bellows acting as the divider. The pump's outlet is coupled by tubing leading to the infusion site. In addition to requiring moving parts, the capillary tube used to dispense the drug at the treatment site is subject to becoming plugged by tissue ingrowth and blood clotting. The device of the Fischell U.S. Pat. No. 4,373,527 incorporates a battery-powered pulsatile pump having inlet and outlet valves and a ceramic filter is employed to filter out contaminants from entering the pump structure. However, there does not appear to be anything to prevent the buildup of clotting materials and/or tissue ingrowth into the outlet port 220 which would ultimately block the flow of medicament from the pump.

OBJECTS

It is accordingly a principal object of the present invention to provide an improved implantable drug delivery apparatus.

Another object of the invention is to provide an improved, implantable drug delivery apparatus having no moving parts.

Still another object of the invention is to provide an improved implantable drug delivery apparatus in which the drug dispensing tube or catheter obviates blockages due to tissue ingrowth.

Still another object is to provide an improved drug delivery apparatus to deliver drug through the anticipated tissue encapsulation or ingrowth which develops around any implanted device following the passage time.

SUMMARY OF THE INVENTION

In accordance with the present invention, there is provided an implantable power source comprising a battery and switching means for selectively and controllably coupling the battery source to a drug delivery catheter. The catheter comprising an elongated flexible plastic tube having a proximal end and a distal end with at least one lumen extending therebetween. The lumen is adapted to be filled with a solution containing the drug to be administered. Also disposed in the lumen and coupled to the power source is a drive electrode. In accordance with one embodiment, there is provided close to the distal end of the catheter a slit which extends totally through the wall thereof so as to communicate with the lumen. The slit is self-sealing and thereby precludes the ingrowth of tissue into the lumen. Positioned proximally of the slit by short predetermined distance on the exterior surface of the catheter is a second electrode which is connected by a conductor extending through the catheter body to a second pole of the power source. The drug to be delivered, when in solution, may be disassociated into charged ions and when the appropriate potential is applied across the internal drive electrode and the external surface electrode, the drug ions are repelled and caused to flow through the slit from the interior of the catheter body towards the exterior electrode and, in doing so, are released into the bloodstream or organ at the location where it is to be utilized. In the event that the drug does not form ions in solution, the drug can still be delivered in this fashion as predicted by the electrokinetic phenomena called electroosmosis.

In accordance with a second embodiment, rather than having a self-sealing slit through the wall of the tube, a larger, permanently open slit is provided near the distal end of the catheter but that slit is shrouded by a membrane capable of transmitting low molecular weight chemicals, e.g., certain drugs, while acting as a barrier to larger molecular weight materials, e.g., blood. Again by appropriately energizing the electrodes, the drug ions are repelled from the driving electrode and forced through the membrane under the influence of the ionic current flow.

As a further feature of the invention, it is contemplated that a salt containing the drug to be administered may be placed in the catheter body to maintain a saturated solution such that when ionized drug molecules are released into the system, they are immediately replaced.

DESCRIPTION OF THE DRAWINGS

The features and working principles of the present invention will be better understood from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
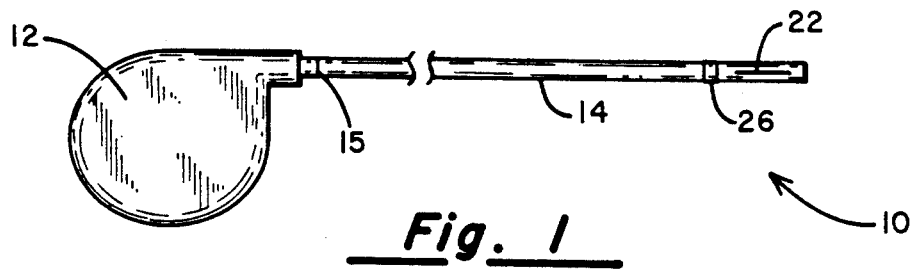
FIG. 1 is a view illustrating the implantable drug delivery system of the present invention.

Referring first to FIG. 1, there is illustrated an overall view of the drug delivery system in accordance with the present invention. It is indicated generally by numeral 10 and seen to include an implantable power source 12 and an elongated flexible plastic tubular catheter 14 connected at its proximal end 15 to the power source 12. The power source may be totally implanted within the body at a convenient site in the same fashion that heart pacer pulse generators are now implanted. In that the invention resides principally in the catheter portion 14, it is felt unnecessary to describe in detail the constructional features of the power source 12. Those skilled in the art will readily envision how the power source may be packaged and protected for long-term placement within the body. Suffice it to say, it will typically include a battery, such as a lithium iodide cell of the type commonly used in empowering implantable pacemaker devices. The power source 12 may also include a switching circuit for selectively coupling the battery terminals to the electrodes on the catheter 14 yet to be described. The use of a magnetic reed switch which can be actuated by appropriately positioning a permanent magnet at a known site external to the body will allow the patient to turn the drug delivery apparatus on and off. The device may also be programmable and microprocessor controlled in such a fashion that when an arrhythmia is detected through the use of the electrodes, operated for purposes of sensing, the delivery of drug can be performed in a predetermined manner.

Figure 2:
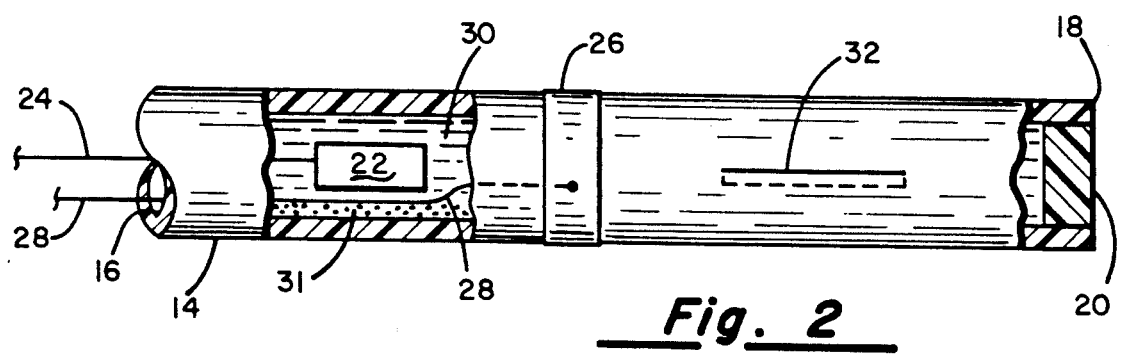
FIG. 2 is a greatly enlarged view of the distal end portion of the drug delivery catheter illrustrated in FIG. 1 in accordance with one embodiment of the invention.

Referring next to FIG. 2 which illustrates a greatly enlarged and partially cross-sectioned view of the indicated distal end portion of the drug delivery catheter of FIG. 1, it is seen to comprise a body member in the form of a tube and including at least one lumen 16 which extends substantially the entire length of the catheter body 14, but which is closed at its distal end 18 by a plug 20. Extending through the wall of the tube 14 and communicating with the lumen 16 is a fine slit 22 which is preferably cut at an angle so as to increase the amount of wall material intersected by the slit 22 to render the slit self-closing and to prevent the ingress of blood or other tissue. Disposed within the lumen 16 of the catheter body 14 is a drive electrode 22 preferably formed from a noble metal or other standard electrode material and having a conductor 24 attached thereto and extending through the lumen to the catheter's proximal end where it connects with the power source 12.

Disposed on the outer surface of the catheter body 14 at a location slightly proximal of the slit 22 is a surface electrode, here shown as a conductive ring 26. A conductor 28, connected at its proximal end to the power source 12 extends through the lumen of the catheter and through the wall thereof to attach to the ring electrode 26.

Either the entire lumen or a predetermined portion thereof is filled with an ionic solution 30 and the solution effectively submerges the drive electrode 22 therein. It is also contemplated that the solution 30 be saturated and in equilibrium with solid phase drug crystals 31 also located within the catheter's lumen. The port or slit 22 formed through the wall of the plastic catheter body is self-healing and does not permit the liquid solution 30 to leak through it. Moreover, blood and cell tissue is incapable of finding its way through the port 22 into the catheter's lumen. This, then, eliminates the possibility of catheter occlusion.

The catheter 14 is dimensioned to be implanted transvenously with the distal end portion shown in FIG. 2 in a venous location or possibly in the right ventricle of the heart. When the drive electrode 22 is powered by the source 12 such that the polarity of the drive electrode 22 matches that of the drug ions in solution, ionic repulsion between the drug and the drive electrode 22 will force the drug molecules through the slit in their effort to reach the oppositely-charged return electrode 26, thereby releasing the drug into the bloodstream at the precise location of the catheter's distal end. In accordance with Farady's Law, the amount of drug released is proportional to the product of current and time, each of which can be precisely controlled to effect a desired dose rate. When drug crystals 31 are also included in the lumen, as drug molecules are driven out of solution through the port 22, the crystals dissolve to maintain the solution in a saturated condition.

Figure 3:
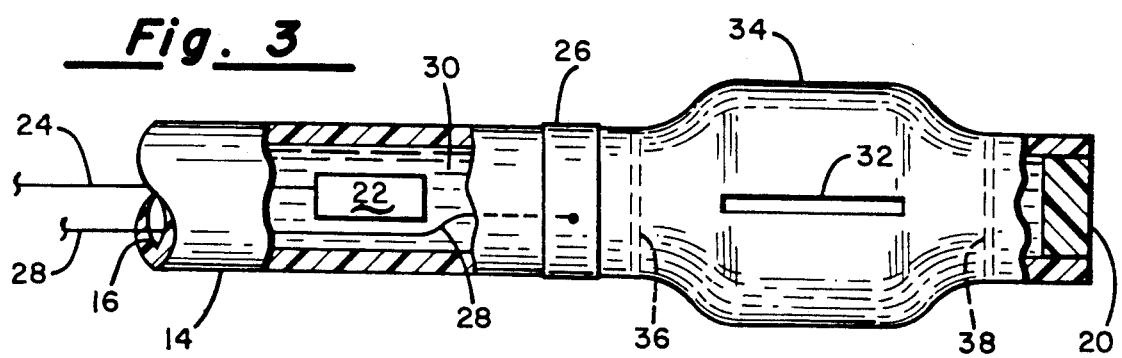
FIG. 3 is a greatly enlarged view of the distal portion of a drug delivery catheter in accordance with an alternative embodiment.

The distal tip design illustrated in FIG. 3 is generally identical to the arrangement shown in FIG. 2, but with two modifications. Rather than having a narrow, self-sealing slit as at 22 in FIG. 2, in the arrangement of FIG. 3 the port through the wall of the catheter body 14 comprises a wider slot 32. Then, a plastic membrane sleeve 34 is bonded to the catheter body as at 36 and 38 in covering relation relative to the port or slot 32. The material of the membrane is selected to have a desired molecular weight cut-off property. More specifically, the film or membrane 34 is selected so as to be a total barrier against the high molecular weight blood clot forming substances such as fibrinogen and thrombin. Thus, the slot 32 and the catheter's lumen will remain patent over prolonged periods of implantation within the body. The membrane is also chosen so as to create a barrier to the outflow of the solution 30 contained within the lumen. It is only when the drive electrode 22 is coupled to the power source 12 so as to be charged to a polarity which is the same as the polarity of the drug ions that sufficient force is created on the drug ions to cause them to pass through the membrane 34 in an electrophoresis process.

In FIG. 3 the membrane 34 is shown as being expanded out relative to the catheter body 14 so as to be more visible in the drawing. It is to be understood, however, that the film 34 can be made to conform tightly to the outside circumference of the catheter. A film suitable for the use in the present application may be approximately 0.001–0.010 inch thick film of cellulose, polycarbonate, or other biocompatible plastics manufactured by techniques known in the dialysis membrane industry.

Figure 4:
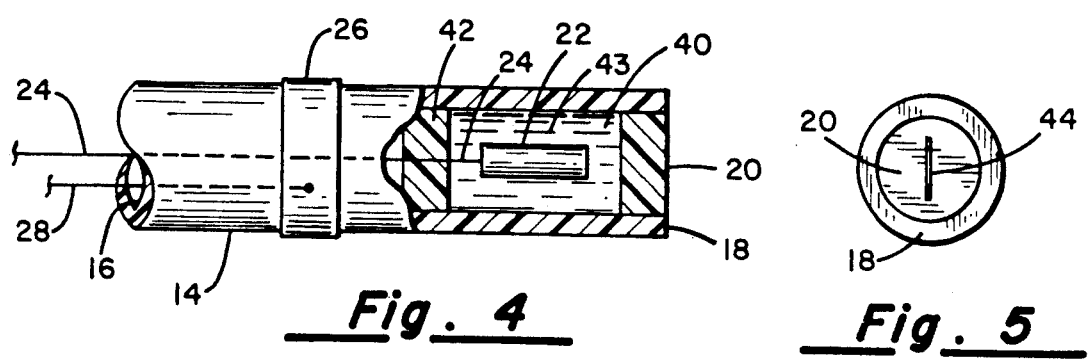
FIG. 4 is a greatly enlarged view of the distal portion of a drug delivery catheter in accordance with a further embodiment.
Figure 5:
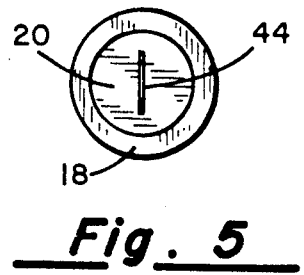
FIG. 5 is an end view of the embodiment of FIG. 4.

FIGS. 4 and 5 illustrate a still further embodiment of the invention. In this latter arrangement, a chamber 40 is formed near the distal end 18 of the tubular member 14 by means of a proximal plug 42 contained within the lumen end and a spaced distal plug 20. Disposed within the chamber 40 is a gel matrix material incorporating the drug to be dispensed. The drive electrode 22 is also contained within the chamber 40 and within the gel material. The conductor 24 leading to the drive electrode 22 passes through the plug or barrier 42 to establish the desired electrical contact. Positioning the electrode within the gel material may not be necessary, however, as long as contact is maintained between the electrode and the drug solution, which is, in turn, in contact with the gel.

FIG. 5 is a distal end view of the device of FIG. 4. As can be seen, the end plug 20 includes a fine slit 44 extending through its thickness dimension. Because of the viscosity of the gel material 42 contained within the chamber 40, it does not flow through the slit. However, when a voltage is applied across the conductors 24 and 28, electrophoresis drives the drug through the slit 44 and into the bloodstream surrounding the distal end portion of the catheter between the slit 44 and the exterior electrode 26.

It can be seen, then, that the present invention provides a means for controllably delivering drugs directly into the vasculature at a desired location and involving no moving parts and whose delivery catheter will remain patent after chronic periods of inactivity. In that the drug molecules are delivered to the body electrically, as opposed to the delivery of a volume of liquid to the body mechanically, no moving parts are required. The catheter itself acts as the drug reservoir and, hence, no additional implantable reservoir need be provided. By including the drug in its crystalline form in the lumen along with the drug solution, the solution will remain saturated following delivery of one or more desired doses. That is to say, following delivery of the drug, the drug and crystalline phase will dissolve into solution and replenish the amount of drug previously delivered to the bloodstream.

Precise control can be maintained over the dosage of the delivered drug in that the amount delivered would be directly proportional to the product of the current flow and the time (Faraday's Law).

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An implantable drug delivery apparatus for long-term implantation within the body of an animal comprising: p1 (a) an implantable source of direct current potential;
    (b) an elongated, flexible plastic tubular catheter body having a proximal end, a distal end and at least one lumen extending from said proximal end to said distal end, and lumens at said distal end being closed, except for a port extending through said catheter body near said distal end;
    (c) first and second electrode means adapted to be connected to said source of direct current potential, said first electrode being contained within said lumen and said second electrode being a ring disposed on the exterior surface of said catheter body; and
    (d) A liquid solution containing a drug in solution substantially filling said sumen and engulfing said first electrode, the connection of said first and second electrodes to said source driving said drug through said port.

2. The apparatus as in claim 1 wherein said port comprises an elongated slit.

3. The apparatus as in claim 1 wherein said ring is located proximally of said port.

4. The apparatus as in claim 1 wherein said port is of a size to prevent blood or tissue intrusion into said lumen and yet permit the outflow of said solution.

5. The apparatus as in claim 4 wherein said port is an elongated narrow slit.

6. The apparatus as in claim 1 and further including a membrane having a predetermined molecular weight cut-off mounted in covering relation to said port.

7. The apparatus as in claim 6 wherein said molecular weight cut-off is such that blood and tissue is incapable of penetrating through said membrane into said port.

8. The apparatus as in claim 7 wherein said membrane is a barrier to the flow of said solution but penetrable by said drug when driven by first and second electrodes.

9. The apparatus as in claim 1 and further including said drug in crystalline form to maintain a saturated condition in said solution upon delivery of said drug through said port.

10. The apparatus as in claim 1 wherein said solution is a gel material.

11. The apparatus as in claim 10 wherein said first electrode is in contact with said gel material.

* * * * *

UNITED STATES PATENT AND TRADEMARK OFFICE
CERTIFICATE OF CORRECTION

PATENT NO. : 5,041,107

DATED : August 20, 1991

INVENTOR(S) : Ronald W. Heil, Jr.

It is certified that error appears in the above-identified patent and that said Letters Patent is hereby corrected as shown below:

Col. 6, line 6, delete "p1" and start a new paragraph with (a).

Col. 6, line 21, change "sumen" to read -- lumen --.

Signed and Sealed this

Twenty-ninth Day of December, 1992

Attest:

DOUGLAS B. COMER

*Attesting Officer*  *Acting Commissioner of Patents and Trademarks*